United States Patent
Guertin et al.

(10) Patent No.: US 7,402,824 B2
(45) Date of Patent: Jul. 22, 2008

(54) PARTICLE BEAM NOZZLE

(75) Inventors: Timothy Guertin, Palo Alto, CA (US); Marcel R. Marc, Palo Alto, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 233 days.

(21) Appl. No.: 11/447,587

(22) Filed: Jun. 5, 2006

(65) Prior Publication Data
US 2008/0067451 A1   Mar. 20, 2008

(51) Int. Cl.
*G21G 1/00* (2006.01)
(52) U.S. Cl. .................................. 250/492.3; 378/65
(58) Field of Classification Search .............. 250/492.3; 378/65
See application file for complete search history.

(56) References Cited

U.S. PATENT DOCUMENTS 7,173,264 B2 * 2/2007 Moriyama et al. ....... 250/492.3
7,280,633 B2 * 10/2007 Cheng et al. .................. 378/65

* cited by examiner

*Primary Examiner*—Kiet T Nguyen
(74) *Attorney, Agent, or Firm*—Carr & Ferrell LLP

(57) ABSTRACT

An improved particle beam treatment system optionally includes exchangeable particle beam nozzles. These particle beam nozzles may be automatically moved from a storage location to a particle beam path or between particle beam paths for use in medical applications. Movement may be achieved using a conveyance, gantry, rail system, or the like. The improved particle beam treatment system optionally also includes more than two alternative particle beam paths. These alternative particle beam paths may be directed to a patient from a variety of different angles and in different planes.

21 Claims, 9 Drawing Sheets

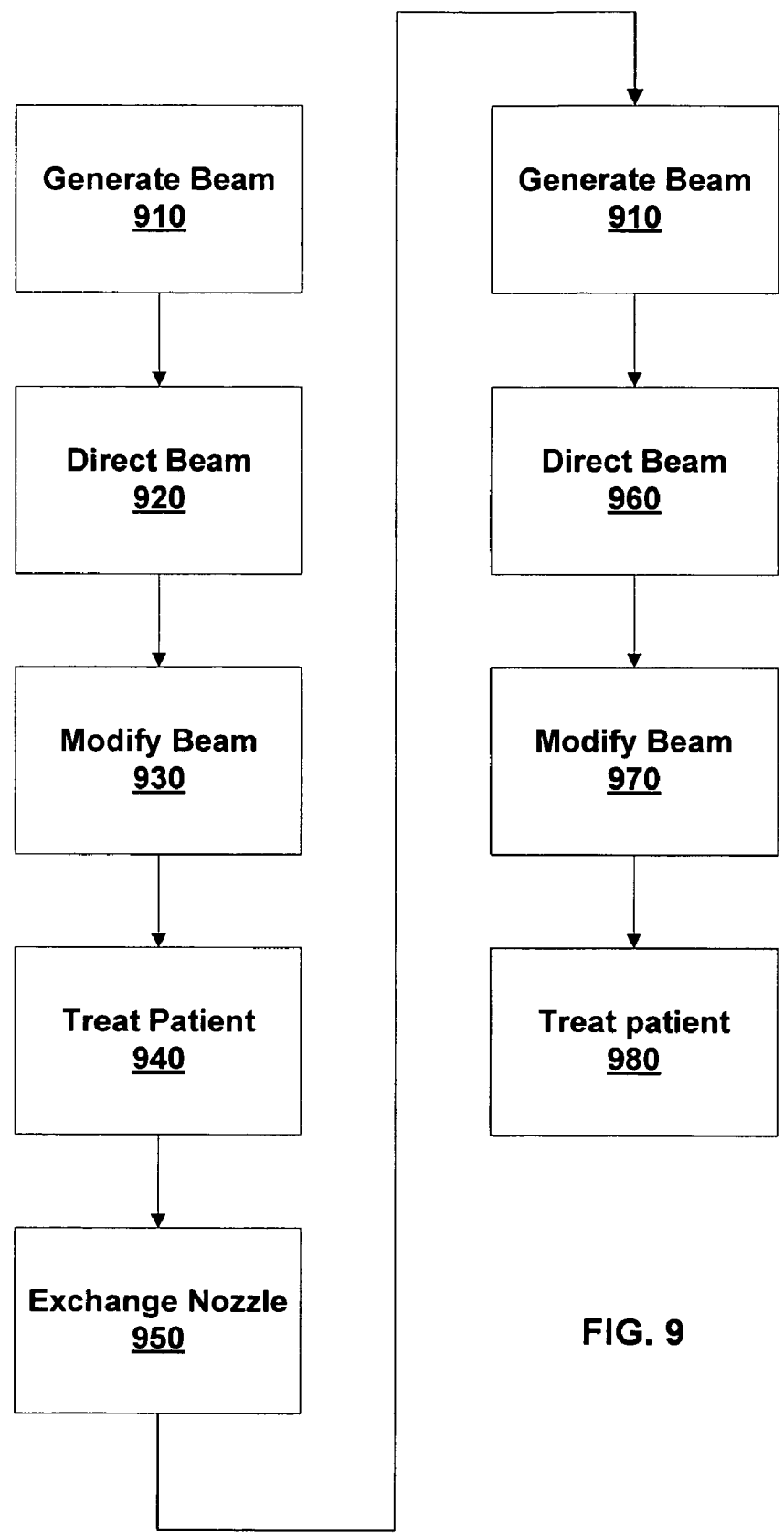

PARTICLE BEAM NOZZLE

BACKGROUND

1. Field of the Invention

The invention is in the field of particle sources and more specifically in the field of particle sources configured for medical applications.

2. Related Art

It has been shown that high-energy particles can be advantageously used for medical treatment of cancer. These high-energy particles typically have energies greater than 20 MeV (million electron volts). For example, protons with energies between 70 MeV and 250 MeV can be used to deposit energy at a very precise depth within a human body.

High-energy protons are generated in a particle accelerator and delivered to a patient at a treatment station. A typical treatment station includes an adjustable gurney or chair configured to position the patient relative to a fixed proton beam. In some instances, the output of the particle accelerator is directed through two alternative paths using particle transport optics such as magnets and electric fields. For example, in one instance a first set of particle transport optics is used to direct protons from above a patient and a second set of particle transport optics is used to direct protons toward the patient from the side at an angle 90 degrees from the first set of particle transport optics. One limitation of this arrangement is that each separate path requires a separate set of expensive particle transport optics and a separate particle beam nozzle.

During a treatment the depth of proton penetration and the position of the proton beam may be varied in order to treat a three dimensional volume within a patient. Depth control is achieved by varying the energy of the protons. This variation can be achieved by passing the protons through varying lengths of an energy adsorbing material or by using a particle source capable of generating particles at selectable energies. The proton beam may be applied over an area perpendicular to the depth dimension by either scanning or scattering the proton beam. Scattering or energy variation of the proton beam is optionally performed in more than one stage. For example, a first scattering step may be applied as the protons leave the particle accelerator and a second scattering step may be applied after the protons pass through final beam steering elements. Two steps are required when the final beam steering elements cannot handle a desired final spatial or energetic distribution.

A path through which particles are transported typically includes a proton nozzle. Proton nozzles can be designed for special purposes, for example, double scattering nozzles, single scattering nozzles, scanning nozzles, and other specialized nozzles known in the art. Different medical treatments require the use of different proton nozzles each weighing one thousand or more pounds and costing hundreds of thousands of dollars. Changing nozzles is a time consuming and labor intensive process that limits the flexibility of treatments particularly between successive patients and causes system downtime.

For the various reasons discussed above, and additional reasons, there is a need for improved sources of high-energy particles.

SUMMARY

Some embodiments include a particle source coupled to three or more alternative beam paths. These alternative beam paths are configured to direct protons or other nuclei toward a patient from a variety of different directions. These different directions may be significantly greater than or less than 90 degrees apart and may be disposed in different planes.

Some embodiments include automated systems and methods of changing particle beam nozzles in a particle beam path and/or changing particle beam nozzles between particle beam paths. For example, various embodiments include a rail system configured to move particle beam nozzles from a first particle beam path to a second particle beam path, from a storage location to a particle beam path, and/or from a first treatment station to a second treatment station.

Particle beam nozzles can be moved into position relative to a particle beam path automatically during a treatment session that includes more than one separate particle dosing of a single patient. Thus, a patient can be treated using more than one type of nozzle during a single treatment session. Further, the same nozzle can be used in more than one particle beam path during the same treatment session.

Although examples discussed herein are related to proton beams, the illustrated embodiments can be applied to other particle beams such as Helium and Carbon beams, etc.

Various embodiments include a system comprising a treatment station for particle beam treatment of a patient, a particle accelerator configured to generate a particle beam, and three or more particle beam paths through which the particle beam can be delivered to the patient at the treatment station, the three or more particle beam paths including at least two particle beam paths significantly greater than 90 degrees apart.

Various embodiments include a system comprising a treatment station for particle beam treatment of a patient, a particle accelerator configured to generate a particle beam for treatment of the patient, and three or more particle beam paths through which the particle beam can be delivered to the patient at the treatment station, the three or more particle beam paths configured such that a first particle beam path is located outside of a plane including a second particle beam path and a third particle beam path.

Various embodiments include a method of treating a patient, the method comprising generating a particle beam of high-energy particles, directing the particle beam of high-energy particles along a first beam path, treating the patient using the particle beam of high-energy particles directed along the first particle beam path, selecting a second particle beam path from among a plurality of alternative particle beam paths different from the first particle beam path, at least one of the plurality of alternative particle beam paths being disposed in part beneath the patient or the first particle beam path laying outside of a plane defined by two of the plurality of alternative particle beam paths, and directing the particle beam of high-energy particles along the second particle beam path.

Various embodiments include a system comprising a first treatment station for particle beam treatment of a patient, a particle accelerator configured to generate a particle beam, a first particle beam path along which the particle beam can be delivered to the patient, a second particle beam path along which the particle beam can be delivered to the patient, a particle beam nozzle configured to modify the particle beam, and a transport system configured to automatically move the particle beam nozzle from the first particle beam path to the second particle beam path.

Various embodiments include a method comprising generating a first particle beam of high-energy particles, directing the first particle beam of high-energy particles along a first particle beam path having first particle beam transport optics, modifying the first particle beam of high-energy particles using a particle beam nozzle, treating a first patient using the first particle beam of high-energy particles modified using the particle beam nozzle, selecting a second particle beam path having second particle beam transport optics, moving the particle beam nozzle from the first particle beam path to the second particle beam path under control of a processing unit, generating a second particle beam of high-energy particles, directing the second particle beam of high-energy particles along the second particle beam path, modifying the second particle beam of high energy particles using the particle beam nozzle, and treating the first patient or a second patient using the second particle beam of high-energy particles modified using the particle beam nozzle.

Various embodiments include a system comprising a treatment station for particle beam treatment of a patient, a particle accelerator configured to generate a particle beam, a first particle beam path through which the particle beam can be delivered to the patient, and a transport system configured to automatically move a first of a plurality of different particle beam nozzles to the first particle beam path, and to separately move at least a second of the plurality of different particle beam nozzles to the first particle beam path.

Various embodiments include a method comprising generating a first particle beam of high-energy particles, directing the first particle beam of high-energy particles along a particle beam path, modifying the first particle beam of high-energy particles using a first particle beam nozzle, treating a first patient using the first particle beam of high-energy particles modified using the first particle beam nozzle, exchanging the first particle beam nozzle for a second particle beam nozzle under control of a processing unit, generating a second particle beam of high-energy particles, directing the second particle beam of high-energy particles along the particle beam path, modifying the second particle beam of high energy particles using the second particle beam nozzle, and treating the first patient or a second patient using the second particle beam of high-energy particles modified using the second particle beam nozzle.

Various embodiments include a system comprising a first particle beam nozzle configured for use in a first treatment type, a second particle beam nozzle configured for use in a second treatment type, a transport system configured to alternatively position under control of a processing unit the first particle beam nozzle and the second particle beam nozzle between a particle accelerator and a treatment station.

Various embodiments include a particle beam nozzle comprising, a mount configured to alternatively hold the particle beam nozzle along each of a plurality of alternative particle beam paths, a positioner configured to automatically position the particle beam nozzle relative to a treatment station or one of the plurality of alternative particle beam paths, and an energy modifier configured to vary an energy of high-energy particles within each of the plurality of alternative particle beam paths.

Various embodiments include a particle beam nozzle comprising a conveyance configured to automatically move the particle beam nozzle to a first particle beam path, a coupler configured to hold the particle beam nozzle relative to the first particle beam path, and a beam scanner configured to scan a particle beam of high-energy particles from the first particle beam path.

Various embodiments include a system comprising a treatment station for particle beam treatment of a patient, a particle accelerator configured to generate a particle beam, and three or more particle beam paths through which the particle beam can be delivered to the patient at the treatment station.

Various embodiments include a system comprising a treatment station for particle beam treatment of a patient, a particle accelerator configured to generate a particle beam, and a first particle beam path configured to deliver the particle beam to the patient from beneath the patient.

BRIEF DESCRIPTION OF THE DRAWINGS

FIG. 9 illustrates a method of operating a treatment system including a particle beam path configured to receive a plurality of alternative particle beam nozzles.

DETAILED DESCRIPTION

Figure 1:
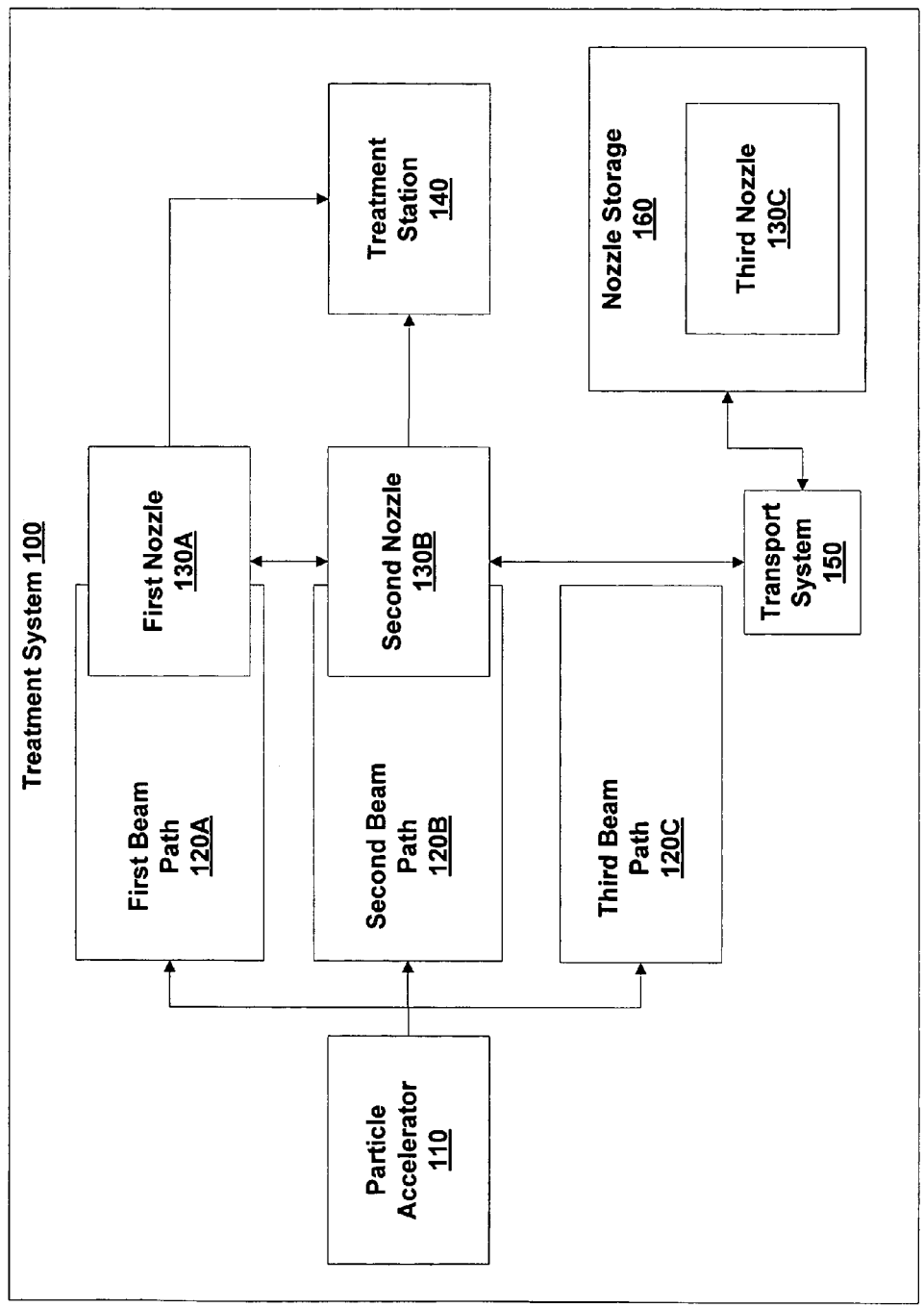
FIG. 1 is a block diagram of a multi-beam path treatment system, according to various embodiments.

Some embodiments include three or more alternative particle beam paths through which a particle beam can be delivered to a particular treatment station. At least part of each particle beam path typically includes a separate set of particle transport optics such as magnets or electric fields. The three or more particle beam paths may lie in a single plane or in two or more different planes. The three or more particle beam paths may also be configured to arrive at the treatment station at a variety of different angular separations.

In some embodiments, the complexity of having multiple particle beam paths is reduced by the inclusion of particle beam nozzles that can be moved from one particle beam path to another automatically, e.g., under control of a processing unit or under the control of a device configured to operate without human intervention. For example, a particular particle beam nozzle may be moved from a first particle beam path to a second particle beam path. This can reduce the number of particle beam nozzles required to support the multiple particle beam paths and thus reduce costs.

The movable particle beam nozzles also allow exchange of particle beam nozzles in a particular particle beam path, which exchange may be automated. For example, in some embodiments, a particle beam nozzle preferred for one type of treatment can easily and quickly be exchanged for a particle beam nozzle preferred for another type of treatment. By making this exchange under control of a processing unit, e.g., under the control of a processor, microprocessor, computer, electronic circuit, electronic controller, and/or the like, with or without software running thereon, the exchange can be performed with minimized downtime and even during a treatment session of a particular patient. As is described further herein, example mechanisms used to transport particle beam nozzles may include support, coupling and positioning elements, as well as a rail system, conveyance, gantry, carrier, belt, carrier, carriage, and/or the like. These mechanisms are typically automated, e.g., some or all of their operations are performed without the need for human intervention. Normally, automated mechanisms operate under the control of a processing unit. The processing unit may include logic configured for selecting a specific particle beam nozzle, selecting a specific particle beam path, controlling movement of the particle beam nozzle, positioning the particle beam nozzle, responding to an interlock, opening or closing a shutter, responding to a collision avoidance parameter, receiving data from a treatment plan, accessing a database including patient information, and/or the like. In various embodiments, the mechanisms used to transport particle beam nozzles are configured to move a particle beam nozzle between particle beam paths or exchange particle beam nozzles at a particle beam path in less than 24 hours, 12 hours, 6 hours, 2 hours, 1 hour, 30 minutes, 15 minutes, 10 minutes, or 5 minutes. Various embodiments include the use of movable particle beam nozzles at treatment stations having one, two, three or more particle beam paths. Automated mechanisms for manipulating particle beam nozzles may be contrasted with manual approaches in which changing of a nozzle could take hours or days, and result in system shutdown over an extended period.

FIG. 1 is a block diagram of a multi-beam path Treatment System 100, according to various embodiments. Treatment System 100 includes at least a Particle Accelerator 110, a First Beam Path 120A, a First Nozzle 130A, and a Treatment Station 140. In various embodiments, Treatment System 100 includes further particle beam paths, such as a Second Beam Path 120B and a Third Beam Path 120C, and/or additional particle beam nozzles, such as a Second Nozzle 130B and a Third Nozzle 130C. First Nozzle 130A, Second Nozzle 130B and Third Nozzle 130C are optionally movable using a Transport System 150 and/or stored in a Nozzle Storage 160.

Particle Accelerator 110 is a source of high-energy particles such as protons, Helium, Carbon, Neon, Argon, and/or some other stable or unstable elemental particle. For example Particle Accelerator 110 can include a cyclotron, synchrotron, linear accelerator, or any other device configured to accelerate particles. In various embodiments, these particles have energy greater than 20, 50, 70, 100, 250 or 500 MeV/u (MeV per nucleon). For example, in one embodiment Particle Accelerator 110 is configured to generate protons with energies between 70 and 250 MeV. These protons are generated in a particle beam having a cross-section as small as 1.0 millimeter (mm), and a kinetic energy distribution as narrow as 1%, 2%, 5%, 20% or 50% of the average particle energy. Such small cross-sections and narrow energy distributions are useful when the particle beam is to be turned or focused. For example, if magnets are used to turn the particle beam, a specific set of magnets will result in a turning radius that is a function of the kinetic energy, particle beams having greater kinetic energy distributions being more difficult to turn without particle loss. However, as discussed further herein, a greater kinetic energy distribution may be desirable when using the particle beam for medical treatment. Therefore, Particle Accelerator 110 optionally includes an energy broadener (e.g., range shifter) and/or a particle beam defocuser (e.g., scatterer) configured to vary the kinetic energy or increase the cross-section of the particle beam, respectively. Such particle beam broadeners and defocusers are known in the art.

First Beam Path 120A, Second Beam Path 120B and Third Beam Path 120C are each particle beam paths through which the particle beam generated using Particle Accelerator 110 may travel to reach an intersection zone at Treatment Station 140. First Beam Path 120A, Second Beam Path 120B and Third Beam Path 120C may each have separate particle beam transport optics. The intersection zone is a zone in which a patient may be placed for treatment and may be a point, area or volume. As is described further herein, First Beam Path 120A, Second Beam Path 120B and Third Beam Path 120C may be configured to direct the particle beam to the intersection zone from a variety of different directions and at a variety of different angles. In some embodiments, these different directions and angles advantageously add flexibility to the treatment of a patient at Treatment Station 140. Each of First Beam Path 120A, Second Beam Path 120B and Third Beam Path 120C can include a variety of steering magnets, collimating elements, or the like. In some embodiments, each of First Beam Path 120A, Second Beam Path 120B and Third Beam Path 120C each include an interface configured to couple with First Nozzle 130A, Second Nozzle 130B and/or Third Nozzle 130C.

First Nozzle 130A, Second Nozzle 130B and Third Nozzle 130C are configured to be disposed along First Beam Path 120, Second Beam Path 120B and/or Third Beam Path 120C. In some embodiments, First Nozzle 130A, Second Nozzle 130B and/or Third Nozzle 130C are each configured to be moved from along one particle beam path to along another particle beam path using Transport System 150. For example, Second Nozzle 130B may be moved from along Second Beam Path 120B to along Third Beam Path 120C using Transport System 150. Alternatively, Second Nozzle 130B may be exchanged for First Nozzle 130A along First Beam Path 120A using Transport System 150. Thus, the particle beam nozzles can be moved between particle beam paths and/or a single particle beam path may receive different particle beam nozzles.

First Nozzle 130A, Second Nozzle 130B and Third Nozzle 130C are configured to modify the particle beam generated using Particle Accelerator 110, optionally in different ways. These modifications can include, for example, scattering, kinetic energy variation, and/or scanning the particle beam. Different particle beam nozzles may be configured to broaden the kinetic energy distribution or otherwise vary the kinetic energy by different amounts and, thus, control a volume within a patient in which treatment is directed. In various embodiments, First Nozzle 130A, Second Nozzle 130B and Third Nozzle 130C include double scattering nozzles, single scattering nozzles, scanning nozzles, or the like.

Treatment Station 140 is configured for treating a patient using the particle beam generated by Particle Accelerator 110 and optionally modified by one of First Nozzle 130A, Second Nozzle 130B and/or Third Nozzle 130C. In some embodiments, Treatment Station 140 includes a patient support such as a platform, harness, chair, gurney, or the like. This patient support typically includes multiple degrees of freedom to position the patient and may be robotic. In some embodiments, Treatment Station 140 includes one or more openings (e.g., removable panels or panels including holes) configured for the particle beam to pass through from beneath the patient. Some embodiments include more than one of Treatment Station 140. These Treatment Station 140 are optionally located in different rooms.

Transport System 150 is configured to move First Nozzle 130A, Second Nozzle 130B and/or Third Nozzle 130C, typically under control of a processing unit. Transport System 150 can include, for example, a processing unit configured to receive information from an encoder, mechanical contact, or other position sensor, a data input configured to receive instructions regarding where a particle beam nozzle should be moved, and logic configured to control the movement of a particle beam nozzle from one particle beam path to another, or the like. As described further herein, different particle beam paths may be associated with (e.g., directed toward) different treatment stations. Thus, Transport System 150 is optionally configured for moving First Nozzle 130A from a position relative to a first Treatment Station 140 to a position relative to a second Treatment Station 140. These first and second Treatment Station 140 can optionally be in different rooms.

Transport System 150 further includes mechanisms for moving a particle beam nozzle. These mechanisms may include, for example, one or more of, a gantry, a system of one or more rails, a motor, a belt, a screw drive, a chain drive, a carriage, hydraulics, a conveyance such as a conveyor or carriage, and/or the like. For example, in some embodiments, Transport System 150 includes a gantry coupled to one or more of First Nozzle 130A, Second Nozzle 130B and Third Nozzle 130C, and configured to move these particle beam nozzles to positions along First Beam Path 120A, Second Beam Path 120B and/or Third Beam Path 120C. The motion of the gantry is optionally circular, in which case positions for the particle beam nozzles along the various particle beam paths may be distributed in a circular fashion around an intersection zone. In some embodiments, Transport System 150 further includes mechanisms for moving a particle beam nozzle in and out of the gantry. In other embodiments, Transport System 150 includes a rail system comprising one, two or more rails configured to support a carriage. The carriage includes a position sensor configured to determine the position of a particle beam nozzle and optionally a positioner configured to make fine adjustments in the position of the particle beam nozzle relative to a particle beam and/or Treatment Station 140.

In various embodiments, Transport System 150 is configured to move a particle beam nozzle from along one particle beam path to along a second particle beam path, or from Nozzle Storage 160 to along a particle beam path in less than 15, 10, 5, 3, or 1 minutes, or less than 45, 30 or 15 seconds. For example, in one specific example, Transport system 150 is configured to move First Nozzle 130A from along First Beam Path 120A to along Second Beam Path 120B, or from Nozzle Storage 160 to along Third Beam Path 120C in less than 15, 10, 5, 3, or 1 minutes, or less than 45, 30 or 15 seconds. Movements between or to other particle beam paths may be accomplished in similar times. Some of these movement times are facilitated by a processing unit included in Transport System 150 and, as such, they may be achieved through automatic movement under processing unit control. Some of these movement times are used to move a particle beam nozzle to more than one particle beam path during a single treatment session without significant downtime.

Transport System 150 optionally includes collision avoidance features. For example, in some embodiments Transport System 150 includes a sensor configured to halt movement of a particle beam nozzle when contact is made between the particle beam nozzle and an unexpected object (e.g., a patient or another particle beam nozzle). This sensor may be electrostatic, mechanical, electromagnetic, optical, or the like. Some or all of these collision avoidance features may be included in a particle beam nozzle. In some embodiments these collision avoidance features are configured to halt or otherwise change movement of the particle beam nozzle prior to an undesirable contact.

In some embodiments, Transport System 150 includes a robot configured to move First Nozzle 130A, Second Nozzle 130B and/or Third Nozzle 130C to specific positions relative to one or more particle beam path. For example, Transport System 150 may include a robotic manipulator arm configured to move particle beam nozzles from one position to another. This robotic manipulator arm is optionally disposed on a movable support.

Optional Nozzle Storage 160 is configured to store First Nozzle 130A, Second Nozzle 130B and/or Third Nozzle 130C when these particle beam nozzles are not disposed along a particle beam path. In some embodiments, Nozzle Storage 160 includes a controlled environment including, for example, a positive pressure atmosphere, or the like. Nozzle Storage 160 optionally includes access for replacement or maintenance of First Nozzle 130A, Second Nozzle 130B and/or Third Nozzle 130C. Nozzle Storage 160 is optionally configured to store particle beam nozzles configured for use at more than one of Treatment Station 140.

While FIG. 1 illustrates three particle beam paths and three particle beam nozzles, alternative embodiments can include greater or fewer numbers of each of these features. For example, some embodiments include only one or two particle beam paths, while some embodiments include four or more alternative particle beam paths. Some embodiments include a single particle beam path configured to include several alternative particle beam nozzles and some embodiments include a single particle beam nozzle configured to be included in different particle beam paths.

Figure 2:
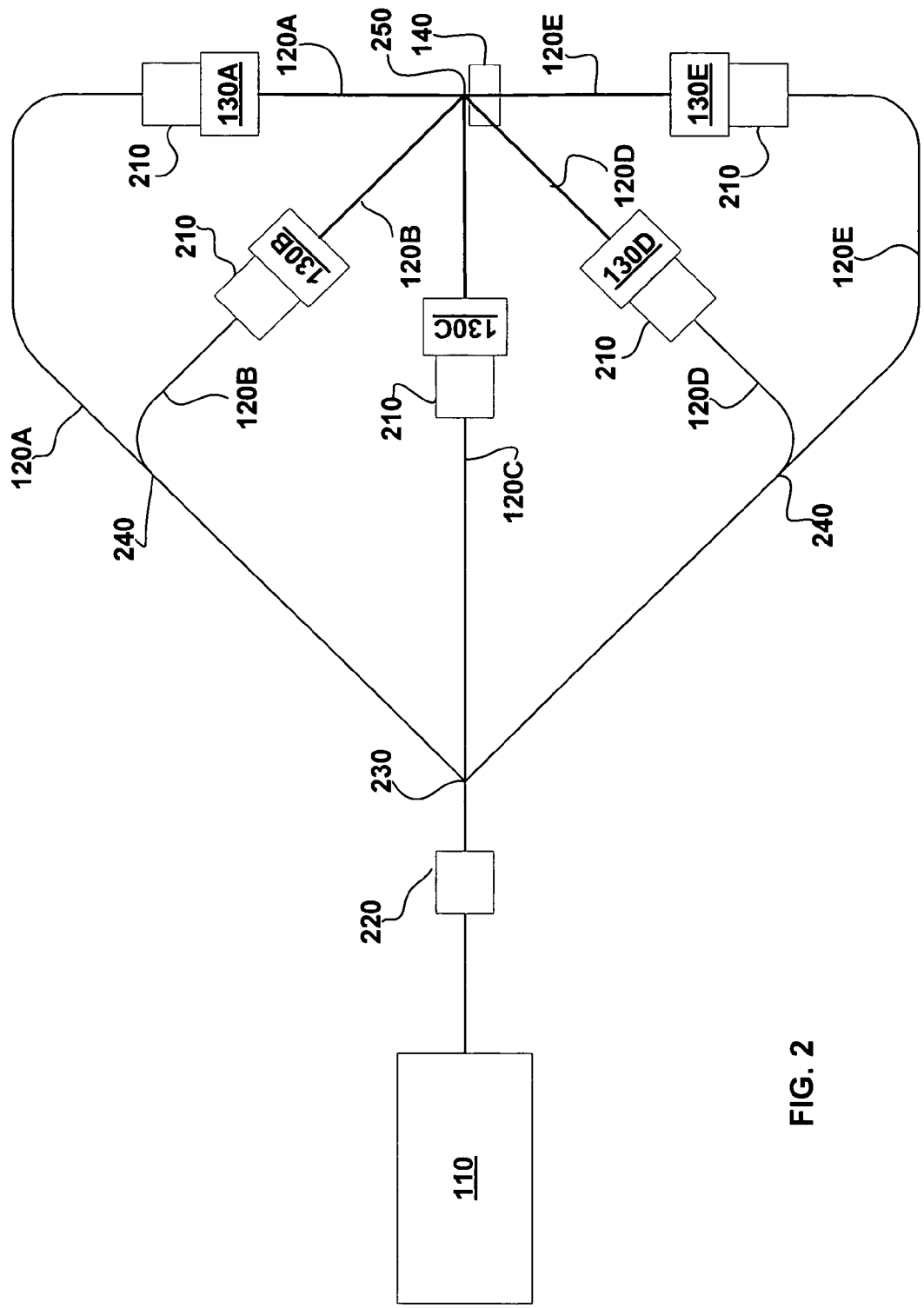
FIG. 2 illustrates a layout of the treatment system of FIG. 1, according to various embodiments.

FIG. 2 illustrates a physical layout of Treatment System 100, according to various embodiments. This illustrated physical layout includes up to five alternative particle beam paths including, for example, First Beam Path 120A, Second Beam Path 120B, Third Beam Path 120C, a Fourth Beam Path 120D and a Fifth Beam Path 120E. Each of these particle beam paths optionally include a particle beam nozzle such as First Nozzle 130A, Second Nozzle 130B, Third Nozzle 130C, a Fourth Nozzle 130D and/or a Fifth Nozzle 130E. Fourth Beam Path 120D and Fifth Beam Path 120E include features and characteristics similar to those of First Beam Path 120A. Likewise, Fourth Nozzle 130D and Fifth Nozzle 130E include features and characteristics similar to those of First Nozzle 130A. Alternative embodiments include more than five alternative particle beam paths.

The particle beam paths illustrated in FIG. 2 are optionally each configured to be coupled to the particle beam nozzles using an Interface 210. In some embodiments, Interface 210 is configured for the attachment of different particle beam nozzles. For example, in some embodiments, Interface 210 includes one or more guide pins configured for the alignment of a particle beam nozzle, such as First Nozzle 130A. In some embodiments, Interface 210 includes a mechanical, electronic or optical encoder or other position sensor configured for determining the position of a particle beam nozzle, such as First Nozzle 130A.

In some embodiments, Interface 210 includes a particle transparent vacuum interface configured for the maintenance of a pressure differential between part of a particle beam path closer to Particle Accelerator 110 and part of the particle beam path closer to Treatment Station 140. Such particle transparent vacuum interfaces are known in the art. Interface 210 optionally includes a shutter configured to be closed to protect the particle transparent vacuum interface when a particle beam nozzle is not disposed in front of a particular Interface 210 and to be opened when a particle beam nozzle is disposed in front of the Interface 210. In these embodiments, each particle transparent vacuum interface is typically protected by either a closed shutter or by a particle beam nozzle. The shutter is optionally automatically opened and closed by the movement of a particle beam nozzle or by Transport System 150.

The embodiments of Transport System 100 illustrated in FIG. 2 further include an optional Beam Conditioner 220 configured to modify the diameter and/or kinetic energy of the particle beam generated by Particle Accelerator 110. Beam Conditioner 220 may be disposed before or after the particle beam paths separate. For example, Beam Conditioner 220 may be disposed along all particle beam paths (as illustrated) or may be disposed such that it is only along First Beam Path 120A and/or Second Beam Path 120B. FIG. 2 illustrates one Trifurcation 230 and two Bifurcations 240 of particle beam paths. In alternative embodiments, different patterns of Trifurcations 230, Bifurcations 240 and/or greater divisions are used to generate 3, 4, 5 or more separate particle beam paths.

Three or more of First Beam Path 120A, Second Beam Path 120B, Third Beam Path 120C, Fourth Beam Path 120D and Fifth Beam Path 120E are optionally coplanar. For example, in some embodiments all five of these particle beam paths lie in the same plane. In alternative embodiments, two, three or four of these particle beam paths lie in the same plane. For the purposes of this discussion, the plane in which a particle beam path lies, angles between particle beam paths, or other aspects of particle beam path orientation are defined by considering those parts of the particle beam paths between Interface 210 and an Intersection Zone 250 disposed at Treatment Station 140.

In some embodiments, two particle beam paths may be approximately collinear and arrive at Treatment Station 140 from opposite directions. Specifically, as illustrated in FIG. 2, First Beam Path 120A and Fifth Beam Path 120E are approximately collinear but arrive at Intersection Zone 250 from opposite directions.

In some embodiments, particle beam paths arrive at Intersection Zone 250 at separations of substantially greater than or less than 90 degrees. For example, both Fourth Beam Path 120D and Fifth Beam Path 120E arrive at Intersection Zone 250 at an angle substantially greater than 90 degrees from First Beam Path 120A, while First Beam Path 120A and Second Beam Path 120B arrive at Intersection Zone 250 at an angle substantially less than 90 degrees. Substantially less than 90 degrees includes less than approximately 80 degrees in some embodiments, less than 70 degrees in further embodiments, and less than 60 degrees in still further embodiments. Substantially greater than 90 degrees includes more than 100 degrees in some embodiments, more than 110 degrees in further embodiments, and more than 120 degrees in still further embodiments. For example, in various embodiments these particle beam paths arrive at angles of at least 100, 110, 120 or 135 degrees. In various embodiments, these particle beam paths arrive at angles of less than 35, 50, 60, 70 or 80 degrees.

In some embodiments, pairs of particle beam paths arrive at Intersection Zone 250 with different angular separations. For example, First Beam Path 120A and Third Beam Path 120C arrive at Intersection Zone 250 with an angular separation of approximately 45 degrees, while Second Beam Path 120B and Fifth Beam Path 120E arrive at Intersection Zone 250 with an angular separation of approximately 135 degrees.

In some embodiments, three different particle beam paths arrive at Intersection Zone 250 spaced approximately 120 degrees from each other. In some embodiments, particle beam paths arrive at Intersection Zone 250 from both below and above a patient. For example, First Beam Path 120A arrives at Intersection Zone 250 from above while Fourth Beam path 120D and Fifth Beam Path 120E arrive at Intersection Zone 250 from below. Part of Fifth Beam Path 120E is, thus, disposed beneath the patient. In some embodiments, Treatment Station 140 includes openings to allow passage of a particle beam from below Treatment Station 140.

Figure 3:
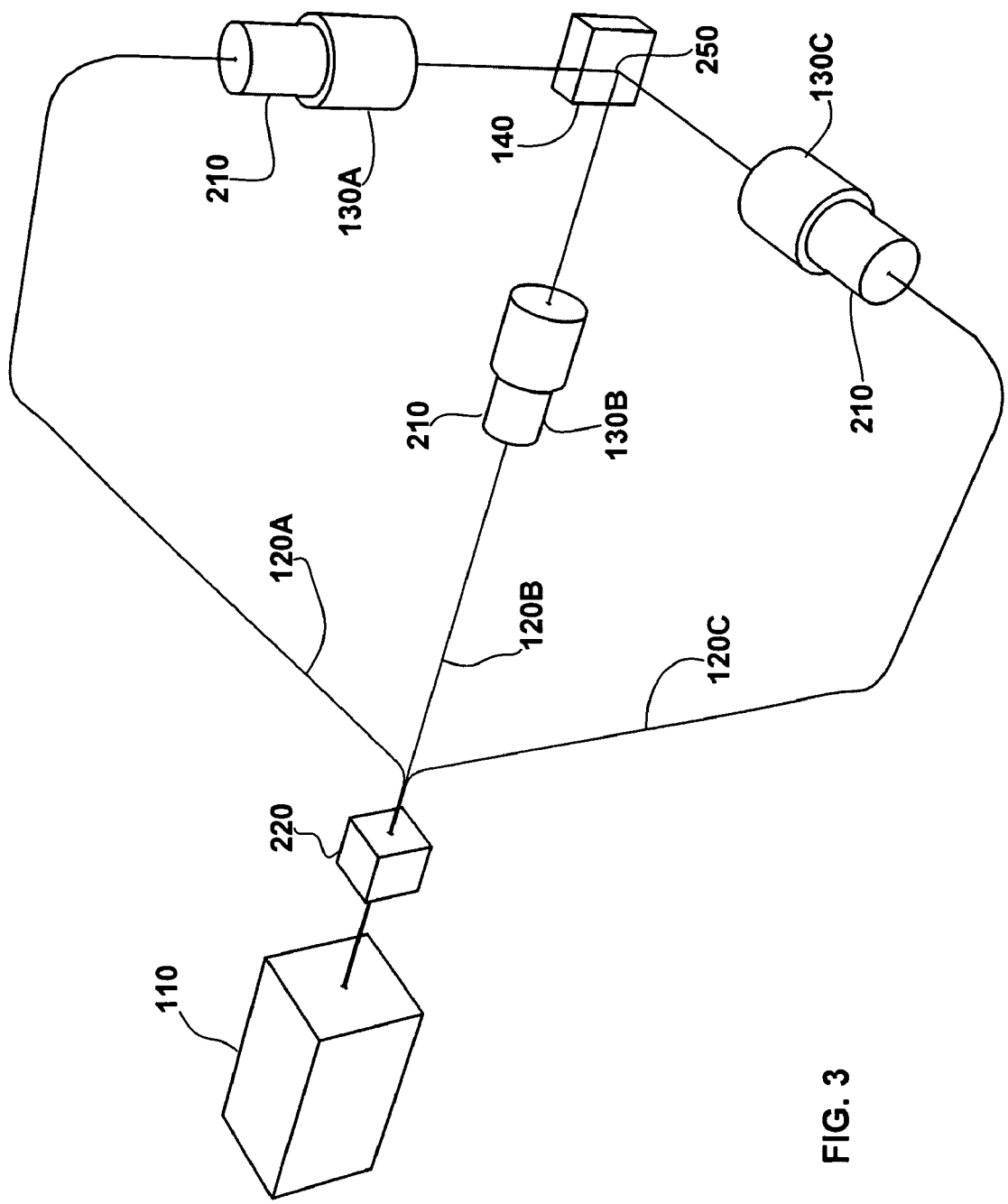
FIG. 3 illustrates an alternative physical layout of the treatment system of FIG. 1, according to various embodiment.

FIG. 3 illustrates an alternative physical layout of Treatment System 100 in a perspective view, according to various embodiments. In these embodiments, three or more particle beam paths arrive at Intersection Zone 250 from along at least two different planes. Specifically, Third Beam Path 120C is not within a plane defined by First Beam Path 120A and Second Beam Path 120B. In some embodiments, First Beam Path 120A, Second Beam Path 120B and Third Beam Path 120C each arrive at Intersection Zone 250 at approximately 90 degrees of each other, as illustrated in FIG. 3.

Figure 4:
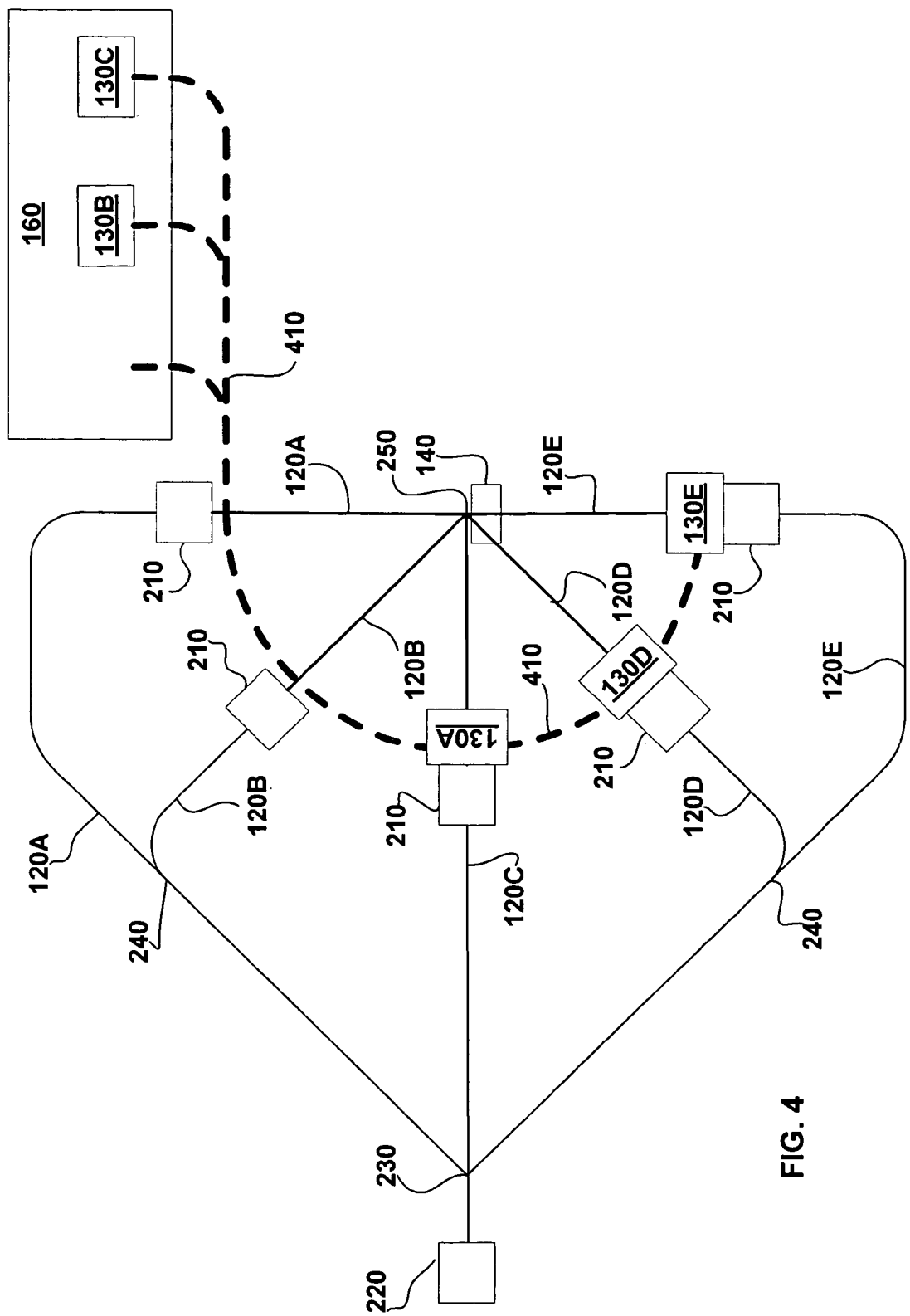
FIG. 4 illustrates an alternative physical layout of the treatment system of FIG. 1 including a rail system, according to various embodiments.
Figure 5:
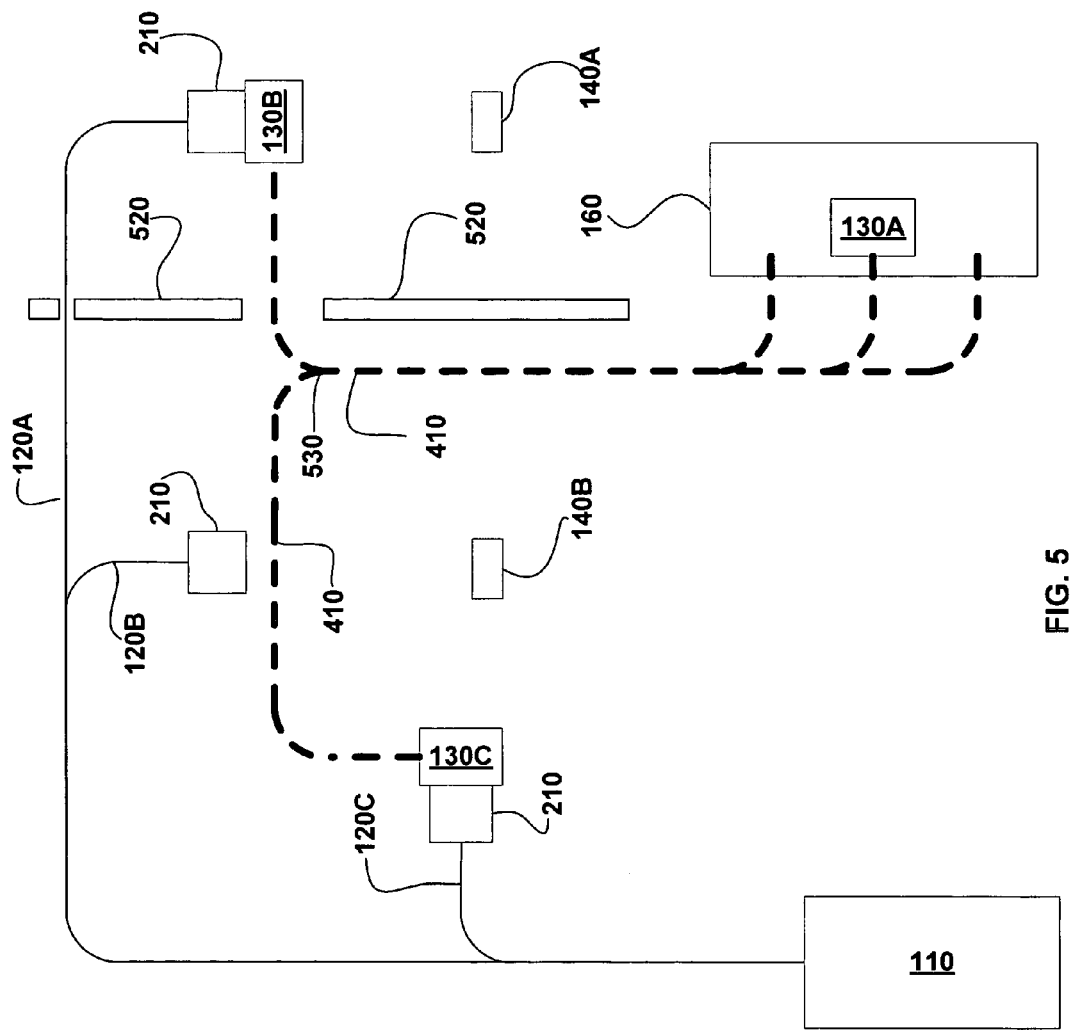
FIG. 5 illustrates an alternative physical layout of the treatment system of FIG. 1 including a plurality of treatment stations, according to various embodiments.

FIG. 4 illustrates an alternative layout of Treatment System 100, according to various embodiments. These embodiments include a Rail System 410 configured to position First Nozzle 130A, Second Nozzle 130B, Third Nozzle 130C, Fourth Nozzle 130D and/or Fifth Nozzle 130E relative to First Beam Path 120A, Second Beam Path 120B, Third Beam Path 120C, Fourth Beam Path 120D and/or Fifth Beam Path 120E. Rail System 410 is optionally further configured to move particle beam nozzles to and from Nozzle Storage 160. In various embodiments, Rail System 410 is included in Transport System 150 and includes a conveyance, a track, a gantry, a system of one or more rails, a motor, a belt, a screw drive, a chain drive, a carriage, hydraulics, and/or the like FIG. 5 illustrates a physical layout of Treatment System 100 including more than one Treatment Station 140, according to various embodiments of the invention. In these embodiments, different particle beam paths are optionally associated with different treatment stations. For example, as illustrated in FIG. 5, First Beam Path 120A is configured for treating a patient at a first Treatment Station 140A, while Second Beam Path 120B and Third Beam Path 120C are configured for treating a patient at a second Treatment Station 140B.

A Barrier 520, such as a radiation shield or wall, optionally separates Treatment Station 140A and Treatment Station 140B. Thus, Treatment Station 140A and Treatment Station 140B may be in different rooms. Rail System 410 is optionally configured for moving particle beam nozzles between particle beam paths associated with different treatment stations and/or between different rooms. Each of these rooms optionally include one, two, three or more particle beam paths. Rail System 410 optionally includes a Switch 530 configured for moving particle beam nozzles to alternative paths of Transport System 150.

Figure 6:
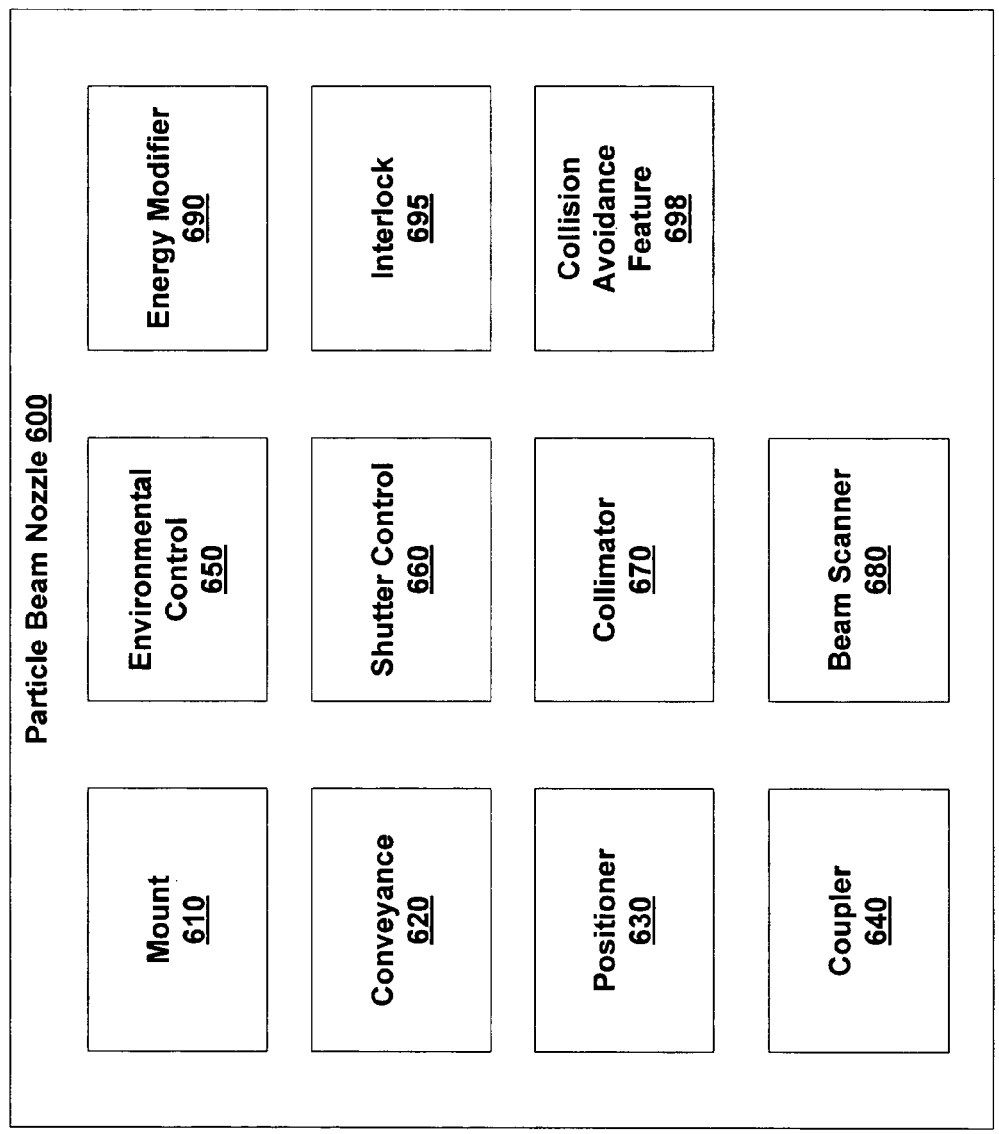
FIG. 6 is a block diagram of a particle beam nozzle, according to various embodiments.

FIG. 6 is a block diagram of a Particle Beam Nozzle 600, according to various embodiments. Particle Beam Nozzle 600 may be included in embodiments of particle beam nozzles, such as First Nozzle 130A, Second Nozzle 130B, Third Nozzle 130C, Fourth Nozzle 130D and/or Fifth Nozzle 130E. Particle Beam Nozzle 600 includes one or more of a Mount 610, an optional Conveyance 620, an optional Positioner 630, and an optional Coupler 640. These features are used for moving, supporting and positioning Particle Beam Nozzle 600 relative to a particle beam path or Treatment Station 140.

Mount 610 is a supporting structure of Particle Beam Nozzle 600 that connects Particle Beam Nozzle 600 to Transport System 150. For example, Mount 610 may include a flange, bolting hardware, guide pins, or the like. In some embodiments, Mount 610 is connected directly to Transport System 150, and in other embodiments, Mount 610 is coupled to Transport System 150 via Conveyance 620.

Conveyance 620 is a vehicle, carriage, cart, trolley, movable platform, or the like, configured to move along Transport System 150. For example, in some embodiments, Conveyance 620 is a self-propelled rail car configured to be coupled to one or more rails of Transport System 150. Conveyance 620 can include a position sensor configured to determine its position along Transport System 150. In some embodiments, Conveyance 620 is part of Transport System 150 rather than Particle Beam Nozzle 600.

Positioner 630 is configured for making fine adjustments in the position of Particle Beam Nozzle 600 relative to a particle beam path or Treatment Station 140. In various embodiments, Positioner 630 is configured to position Particle Beam Nozzle 600 to an accuracy of 0.005, 0.01, 0.1, 0.2, 0.5 or 1.0 mm. Positioner 630 may include stepper motors, hydraulics, piezoelectric devices (PZTs) or the like. For example, in some embodiments, Positioner 630 is configured to move Particle Beam Nozzle 600 using a combination of stepper motors and hydraulics. In some embodiments, Particle Beam Nozzle 600 is first moved along a particle beam path using Conveyance 620 and then more precisely positioned using Positioner 630.

Coupler 640 is configured to attach Particle Beam Nozzle 600 to Interface 210. For example, Coupler 640 may include locking mechanisms, clamps, guide pins, bolts, or the like. In some embodiments, Coupler 640 is configured to assure that Particle Beam Nozzle 600 is precisely positioned. Coupler 640 is optional, for example, in embodiments wherein Particle Beam Nozzle 600 does not make physical contact with Interface 210 or parts of a particle beam path.

In some embodiments, Coupler 640 is configured to be moved relative to other parts of Particle Beam Nozzle 600. For example, in one embodiment, Coupler 640 is configured to move relative to Conveyance 620. As such, Conveyance 620 may be used to move Particle Beam Nozzle 600 close to Interface 210 and then while Conveyance 620 is held in a fixed position, Coupler 640 may be moved to attach to Interface 210. By moving Coupler 640 independently from Conveyance 620, Coupler 640 has the freedom of movement to respond to guide pins or other alignment features when attaching to Interface 210.

Particle Beam Nozzle 600 optionally includes an Environmental Control 650 configured for controlling an environment within part of Particle Beam Nozzle 600. Environmental Control 650 may be configured to maintain part of Particle Beam Nozzle 600 at a reduced pressure, to maintain part of Particle Beam Nozzle 600 in a Helium atmosphere, or the like. Typically, Environmental Control 650 is moved between particle beam paths along with other parts of Particle Beam Nozzle 600.

Particle Beam Nozzle 600 optionally includes a Shutter Control 660 configured to open and close a shutter included in Interface 210. For example, Shutter Control 660 may be configured to open a shutter when Particle Beam Nozzle 600 is moved along a particle beam path and to close the shutter when Particle Beam Nozzle 600 is moved out of the particle beam path. Shutter Control 660 can be a mechanical, electrical or optical mechanism. For example, Shutter Control 660 may include a protrusion configured to physically move the shutter when Coupler 640 is connected to Interface 210. Shutter Control 660 may include an electrical connection, a radio frequency identification (RFID) tag or bar code detectable by Interface 210 and configured to cause Interface 210 to move the shutter. Shutter Control 660 is optionally configured to be responsive to an interlock discussed elsewhere herein.

Particle Beam Nozzle 600 optionally includes a Collimator 670. Collimator 670 may be a multi-leaf collimator, a micro multi-leaf collimator a fixed collimator, or the like. In some embodiments, Transport System 150 is configured to move Collimator 670 independently from other parts of Particle Beam Nozzle 600. Thus, Transport System 150 is optionally configured to move Collimator 670 into and out of a particle beam path separately from Particle Beam Nozzle 600. In some embodiments, Nozzle Storage 160 is configured for insertion of Collimator 670 into a particle beam nozzle.

Particle Beam Nozzle 600 optionally includes a Beam Scanner 680 configured to scan a particle beam in a zone close to Treatment Station 140. Particle Beam Nozzle 600 optionally includes an Energy Modifier 690 configured to vary the kinetic energy of a particle beam.

Energy Modifier 690 may be configured to vary the kinetic energy in a spatial and/or time dependent manner. For example, in some embodiments, Energy Modifier 690 includes a bolus configured for controlling the energy of particles in a spatial manner. Collimator 670, Beam Scanner 680 and/or Energy Modifier 690 are optionally movable independently of other parts of Particle Beam Nozzle 600 using Transport System 150. As such, they may be automatically added to or removed from Particle Beam Nozzle 600. In some embodiments, Nozzle Storage 160 includes features configured for performing this automatic addition or removal.

In some embodiments, Particle Beam Nozzle 600 includes an Interlock 695 configured to ensure that the proper particle beam nozzle is disposed between Particle Accelerator 110 and Interaction Zone 250, and/or configured to ensure that the particle beam nozzle is properly positioned relative to a particle beam path. Interlock 695 can be mechanical, electrical, magnetic, optical, and/or the like. In some embodiments, Interlock 695 includes identifying features configured to identify the particle beam nozzle. This identifying feature may include a bar code, radio frequency identifying tag, electronic circuit, electronic characteristic, magnetic characteristic, optical characteristic, and/or the like. In some embodiments, all or part of Interlock 695 is included in Transport System 150, Interface 210 and/or other parts of Treatment System 100. In some embodiments, Interlock 695 is configured to assure that a correct component, such as Collimator 670, Beam Scanner 680, and/or Energy Modifier 690, is within a particle beam nozzle as required by a treatment plan for a specific patient. Interlock 695 optionally uses patient identity information for this purpose. For example, Interlock 695 may be configured to receive data from a barcode or radio frequency identification tag worn by a patient or from a database system before applying a particle beam to the patient. Particle Beam Nozzle 600 optionally includes a plurality of interlocks such as Interlock 695. For example, a first Interlock 695 configured to assure that a shutter is closed before moving a particle beam nozzle, a second Interlock 695 configured to assure that a correct particle beam nozzle is placed along a particle beam path, and a third Interlock 695 configured to assure that the proper patient is positioned at Treatment Station 140.

Particle Beam Nozzle 600 optionally includes a Collision Avoidance Feature 698 discussed elsewhere herein.

Figure 7:
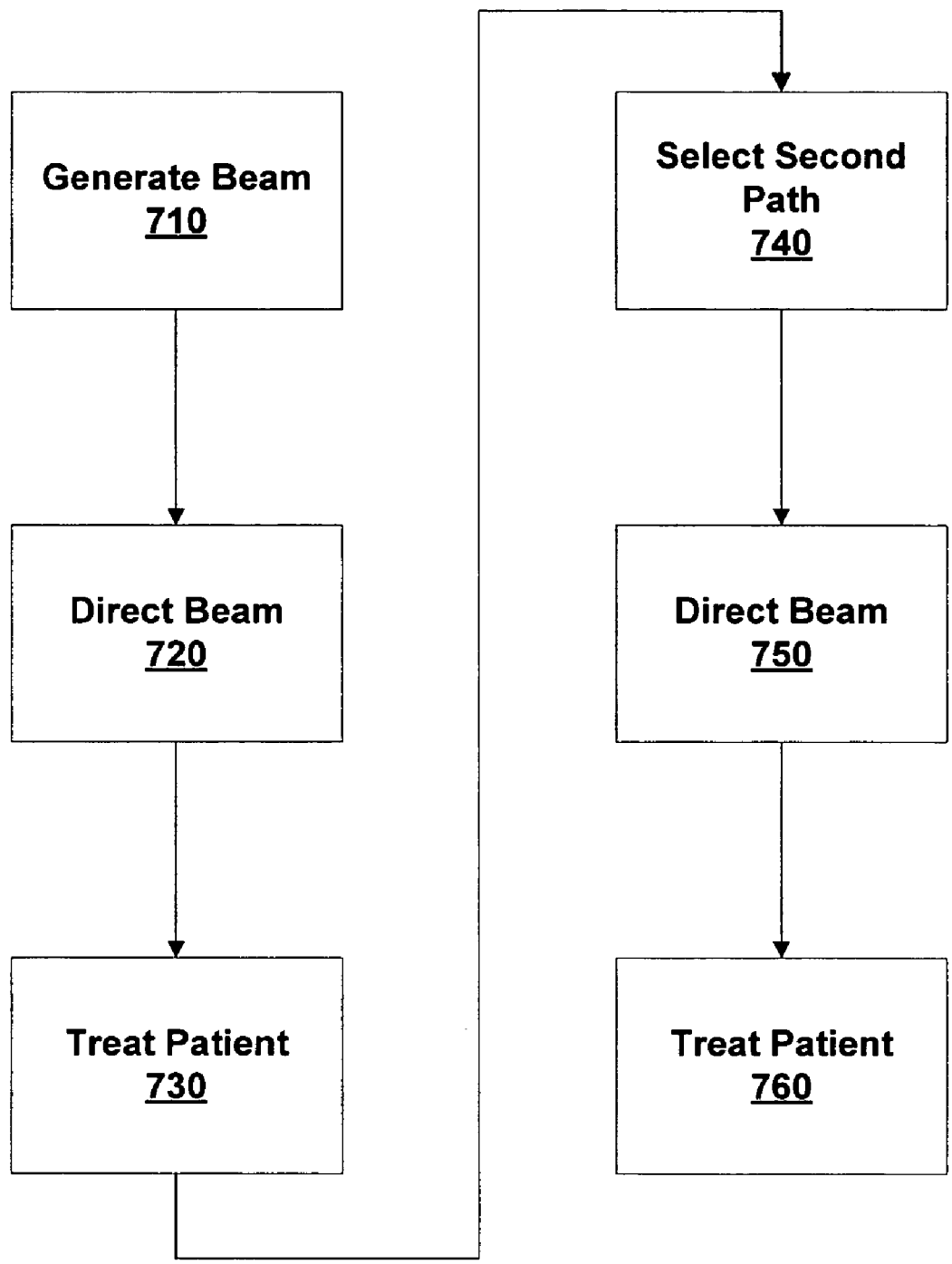
FIG. 7 illustrates a method of operating a treatment system including a plurality of alternative particle beam paths, according to various embodiments.

FIG. 7 illustrates a method of operating a treatment system including a plurality of alternative particle beam paths, according to various embodiments. In this method, a beam of high-energy particles is directed through a plurality of alternative particle beam paths in order to treat one or more patients.

In a Generate Beam Step 710, a particle beam is generated using Particle Accelerator 110. This particle beam may include protons at high energies, e.g., greater than 20 MeV. Alternatively, this particle beam may include Helium, Carbon or other types of nuclei.

In a Direct Beam Step 720, the particle beam generated in Generate Beam Step 710 is directed along a first particle beam path, such as First Beam Path 120A. The first particle beam path typically includes electric or magnetic fields and/or other particle transport optics configured to steer the particle beam toward Treatment Station 140. In a Treat Patient Step 730, the particle beam directed along the first particle beam path is used to treat a patient at the treatment station.

In a Select Second Path Step 740, a second particle beam path is selected from among a plurality of alternative particle beam paths different from the first particle beam path. The plurality of alternative particle beam paths may include, for example, Second Particle Beam Path 120B, Third Particle Beam Path 120C, and/or other particle beam paths discussed herein. One of the alternative particle beam paths is optionally significantly more that 90 degrees from the first particle beam path. For example, in one embodiment one of the alternative particle beam paths is 110 degrees or greater from the first particle beam path. One of the alternative particle beam paths is optionally configured to arrive at the treatment station from below the patient.

In a Direct Beam Step 750, the particle beam generated in Generate Beam Step 710 is directed through the particle beam path selected in Select Second Path Step 740. In a Treat Patient Step 760, the patient is treated using the particle beam directed through the selected particle beam path. The patient is optionally moved between Treat Patient Step 730 and Treat Patient Step 760. In some embodiments, different patients are treated in Treat Patient Step 730 and Treat Patient Step 760

Figure 8:
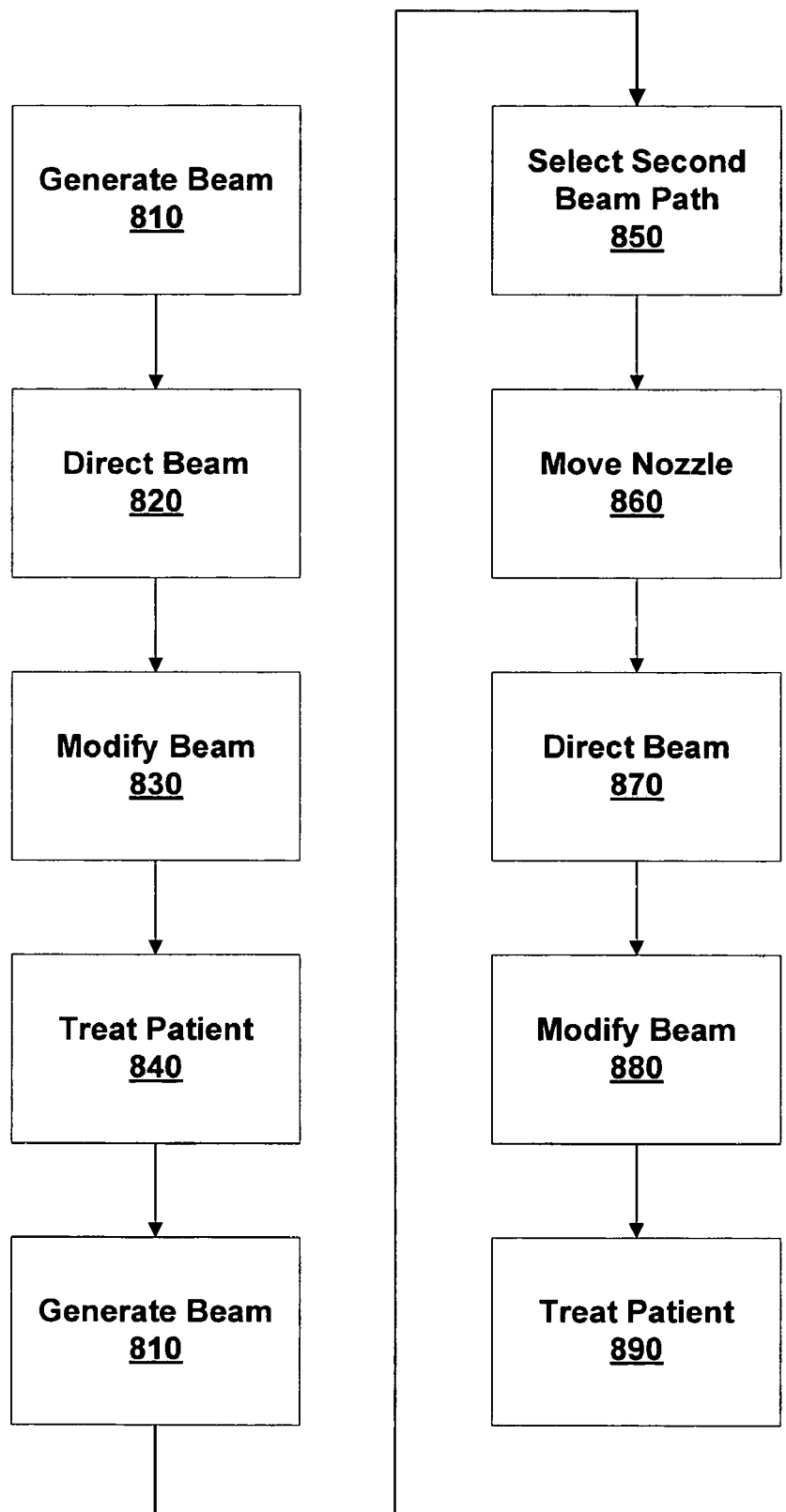
FIG. 8 illustrates a method of operating a treatment system including a particle beam nozzle configured to be moved between alternative particle beam paths, according to various embodiments.

FIG. 8 illustrates a method of operating a treatment system including a particle beam nozzle configured to be moved between alternative particle beam paths, according to various embodiments. In this method, a particle beam nozzle is moved from one particle beam path to another particle beam path for the treatment of a patient. In a Generate Beam Step 810, a particle beam is generated. Generate Beam Step 810 is an embodiment of Generate Beam Step 710.

In a Direct Beam Step 820, the particle beam generated in Generated Beam Step 810 is directed through a first particle beam path such as First Beam Path 120A. In a Modify Beam Step 830, the particle beam directed through the first particle beam path in Direct Beam Step 820 is modified using a particle beam nozzle, such as First Nozzle 130A. This modification can include changes in direction, kinetic energy, dispersion, beam diameter, or the like. For example, in one embodiment, the modification includes changing the direction of the particle beam in order to scan the particle beam over a treatment zone. In a Treat Patient Step 840, the particle beam modified in Modify Beam Step 830 is used to treat a patient at a treatment station.

In a Select Second Beam Path Step 850, a second particle beam path is selected. This particle beam path may be directed at the same treatment station as the first particle beam path, or at a different treatment station. The second particle beam path may be, for example, Second Beam Path 120B or Third Beam Path 120C, or other particle beam paths discussed herein.

In a Move Nozzle Step 860, the particle beam nozzle used to modify the particle beam in Modify Beam Step 830 is moved to the second particle beam path using Transport System 150. This movement is optionally performed using a processing unit. For example, a processing unit may be used to control the movement using the transport system and/or the processing unit may be used to position the particle beam nozzle precisely relative to the second particle beam path. The particle beam nozzle is optionally moved from one room to another room. The particle beam nozzle is optionally moved from above to below a patient.

In a repeat of Generate Beam Step 810, the particle beam is again generated. In some embodiments, a single particle beam is generated continuously throughout the steps illustrated in FIG. 8. Thus, the repeat of Generate Beam Step 810 may be a continuation of the first Generate Beam Step 810. In other embodiments, the generation of a particle beam is halted during at least Move Nozzle Step 860, and then the particle beam is again generated in the repeat of Generate Beam Step 810.

In a Direct Beam Step 870, the particle beam is directed through the second particle beam path. In a Modify Beam Step 880, the particle beam directed through the second particle beam path is modified using the particle beam nozzle. This modification is optionally the same as the modification of Modify Beam Step 830 and is made using the particle beam nozzle moved in Move Nozzle Step 860.

In a Treat Patient Step 890, a patient is treated using the particle beam modified in Modify Beam Step 880. This patient may be the same patient treated in Treat Patient Step 840 or a different patient. If the same patient, then the patient is optionally moved between Treat Patient Step 840 and Treat Patient Step 890. In various embodiments, Treat Patient Step 840 and Treat patient Step 890 occur within 15, 10, 5 or 2 minutes of each other.

FIG. 9 illustrates a method of operating a treatment system including a particle beam path configured to receive a plurality of alternative particle beam nozzles. In this method, two different particle beam nozzles are used to modify a particle beam passed through a single particle beam path. In a Generate Beam Step 910, a first particle beam is generated. Generate Beam Step 910 is an embodiment of Generate Beam Step 710. In a Direct Beam Step 920, the first particle beam generated in Generate Beam Step 910 is directed through a particle beam path, such as First Beam Path 120A.

In a Modify Beam Step 930, the particle beam directed through a particle beam path in Direct Beam Step 920 is modified using a first particle beam nozzle, such as First Nozzle 130A. This modification may include changes in direction, dispersion, kinetic energy, beam diameter, or the like. For example, in one embodiment, the modification includes changing the kinetic energy in order to control a depth of treatment. In a Treat Patient Step 940, a patient is treated using the particle beam modified in Modify Beam Step 930.

In an Exchange Nozzle Step 950, the first particle beam nozzle is exchanged for a second particle beam nozzle, such as Second Nozzle 130B, using Transport System 150. In some embodiments, this exchange is made while the patient is at Treatment Station 140. In various embodiments, this exchange is made in less than 15, 10, 5, or 2 minutes. The second particle beam nozzle is typically configured to modify the particle beam in a different manner or to a different degree than the first particle beam nozzle. Exchange Nozzle Step 950 is optionally performed under control of a processing unit. For example, in some embodiments, a processing unit is used to remove the first particle beam nozzle from the particle beam path and/or a processing unit is used to assure that the second particle beam nozzle is positioned correctly in the particle beam path.

In a repetition of Generate Beam Step 910, a second particle beam is generated using Particle Accelerator 110. As with the repeat of Generate Beam Step 810, the repetition of Generate Beam Step 910 may be an interrupted or uninterrupted continuation of the first Generate Beam Step 910.

In a Direct Beam Step 960, the second particle beam is directed through the particle beam path. In a Modify Beam Step 970, the second particle beam is modified using the second particle beam nozzle. This modification may include changes in direction, dispersion, kinetic energy, beam diameter, or the like.

In a Treat Patient Step 980, the particle beam modified in Modify Beam Step 970 is used to treat a patient. This patient may be the same patient treated in Treat Patient Step 940 or a different patient. If the same patient, the patient is optionally moved between Treat Patient Step 940 and Treat Patient Step 980.

Several embodiments are specifically illustrated and/or described herein. However, it will be appreciated that modifications and variations are covered by the above teachings and within the scope of the appended claims without departing from the spirit and intended scope thereof. For example, while processing unit control of Transport System 150 is discussed herein, all or part of Transport System 150 may be manual. Further, the labeling of particle beam paths and particle beam nozzles within the figures is for illustrative purposes only. Thus, attributes applied to one particle beam path or one particle beam nozzle may be applied to other particle beam paths or other particle beam nozzles. For example, while First Beam Path 120A is shown as coming from above Treatment Station 140 and Beam Path 120E is shown as coming from below Treatment Station 140, these labels and/or positions may be reversed.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated. In general, features or aspects shown or discussed in relation to one embodiment are not limited to that embodiment and can be used in different embodiments, and each embodiment need not contain each feature shown or described in relation to that embodiment.

What is claimed is:

1. A particle beam nozzle comprising:
   a mount configured to alternatively hold the particle beam nozzle along each of a plurality of alternative particle beam paths; and
   a positioner configured to automatically position the particle beam nozzle relative to a treatment station or one of the plurality of alternative particle beam paths.

2. The particle beam nozzle of claim 1, further comprising a collimator configured to collimate high-energy particles.

3. The particle beam nozzle of claim 1, further comprising a conveyance configured for moving the particle beam nozzle between the plurality of alternative particle beam paths.

4. The particle beam nozzle of claim 1, further comprising a coupler configured for connecting the particle beam nozzle to part of one of the plurality of alternative particle beam paths.

5. The particle beam nozzle of claim 1, further including an environmental control configured to be moved with the particle beam nozzle between the plurality of alternative particle beam paths.

6. The particle beam nozzle of claim 1, wherein the particle beam nozzle is a double scattering nozzle.

7. The particle beam nozzle of claim 1, wherein the particle beam nozzle is a scanning nozzle.

8. The particle beam nozzle of claim 1, further including a shutter control configured to open or close a shutter along one of the plurality of alternative particle beam paths.

9. The particle beam nozzle of claim 1, further including a shutter control responsive to an interlock.

10. The particle beam nozzle of claim 1, further including an energy modifier configured to vary an energy of high-energy paticles within each of the plurality of alternative particle beam paths.

11. The particle beam nozzle of claim 10, wherein the energy modifier is configured to be added to or removed from the particle beam nozzle using an automated transport system.

12. A particle beam nozzle comprising:
    a conveyance configured to automatically move the particle beam nozzle to a first particle beam path;
    a coupler configured to hold the particle beam nozzle relative to the first particle beam path; and
    a beam scanner configured to scan a particle beam of high-energy particles from the first particle beam path.

13. The particle beam nozzle of claim 12, wherein the conveyance is further configured for moving the particle beam nozzle between alternative particle beam paths.

14. The particle beam nozzle of claim 12, wherein the conveyance is further configured to move the particle beam nozzle to a second particle beam path.

15. The particle beam nozzle of claim 12, wherein the conveyance is further configured to move the particle beam nozzle from a nozzle storage to the first particle beam path.

16. The particle beam nozzle of claim 12, further including a positioner configured to automatically position the particle beam nozzle relative to a treatment station or the first particle beam path.

17. The particle beam nozzle of claim 12, further comprising a collimator configured to collimate the high-energy particles.

18. The particle beam nozzle of claim 12, wherein the particle beam nozzle is a single scattering nozzle.

19. The particle beam nozzle of claim 12, further comprising a collimator configured to collimate the high-energy particles, the collimator being configured to be separated from the particle beam nozzle using a transport system.

20. The particle beam nozzle of claim 12, further including a collision avoidance feature configured to change movement of the particle beam nozzle.

21. The particle beam nozzle of claim 12, wherein the beam scanner is configured to be added to or removed from the particle beam nozzle using an automated transport system.

* * * * *